United States Patent [19]

Wunder et al.

[11] Patent Number: 4,902,823

[45] Date of Patent: Feb. 20, 1990

[54] PROCESS FOR THE PREPARATION OF VINYL ACETATE

[75] Inventors: Friedrich Wunder, Flörsheim am Main; Günter Roscher, Kelkheim; Klaus Eichler, Eschborn, all of Fed. Rep. of Germany

[73] Assignee: Hoechst Aktiengesellschaft, Frankfurt/Main, Fed. Rep. of Germany

[21] Appl. No.: 307,733

[22] Filed: Feb. 7, 1989

[30] Foreign Application Priority Data

Feb. 9, 1988 [DE] Fed. Rep. of Germany ....... 3803900

[51] Int. Cl.$^4$ .......................................... C07C 67/055
[52] U.S. Cl. .................................................. 560/245
[58] Field of Search ........................................ 560/245

[56] References Cited

U.S. PATENT DOCUMENTS

| 3,939,199 | 2/1976 | Fernholz et al. | 560/245 |
| 4,048,096 | 9/1977 | Bissot | 560/245 |
| 4,087,622 | 5/1978 | Nakamura | 560/245 |
| 4,370,492 | 1/1983 | Wunder | 560/245 |
| 4,668,819 | 5/1987 | Fernholz et al. | 560/245 |

*Primary Examiner*—Michael L. Shippen

[57] ABSTRACT

The invention relates to a process for the preparation of vinyl acetate in the gas phase from ethylene, acetic acid and oxygen or oxygen-containing gases on a catalyst which contains palladium and/or compounds thereof and if appropriate additionally gold and/or gold compounds and, as activators, alkali metal compounds and if appropriate additionally cadmium compounds, on a support. The support consists of cylindrical particles with curved front faces. The support material is aerogenic $SiO_2$ or an aerogenic $SiO_2$-$Al_2O_3$ mixture having a surface area of 50–250 m$^2$/g and a pore volume of 0.4–1.2 ml/g, which is formed to the extent of at least 50% by pores having a diameter of 50–200 Å.

3 Claims, 1 Drawing Sheet

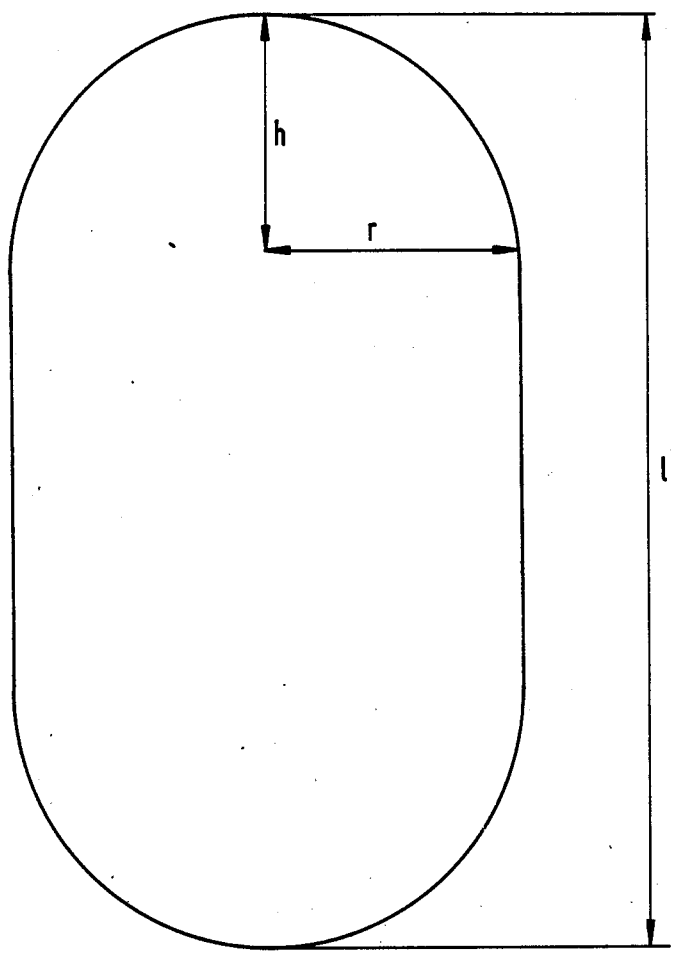
FIG.

PROCESS FOR THE PREPARATION OF VINYL ACETATE

It is known that ethylene can be reacted in the gas phase with acetic acid and oxygen or oxygen-containing gases on fixed bed catalysts to give vinyl acetate. Suitable catalysts contain a noble metal content and an activator content. The noble metal content preferably consists of palladium and/or compounds thereof; gold and/or compounds thereof can additionally also be present (U.S. Pat. No. 3,939,199, DE-OS No. 2,100,778 and U.S. Pat. No. 4,668,819). The activator content here consists of compounds of elements of main group 1 and/or of main group 2 and/or cadmium. Potassium is the preferred element of main group 1. These active components are applied in finely divided form to supports, silicic acid or aluminum oxide in general being used as the support material.

The specific surface area of the supports is in general 40–350 m$^2$/g. According to U.S. Pat. No. 3,939,199, the total pore volume should be 0.4–1.2 ml/g, and less than 10% of this volume should be formed by "micropores" having a pore diameter of less than 30 Ångströms. Examples of suitable supports with these properties are aerogenic SiO$_2$ or an aerogenic SiO$_2$-Al$_2$O$_3$ mixture. The support particles for the preparation of vinyl acetate are in general in the shape of beads. However, tablets and cylinders have also already been used.

In comparison with the spherical supports which have been most frequently used industrially to date and consist of calcined bentonite which has been washed with acid, the regular cylinders (that is to say those with flat front faces) of aerogenic SiO$_2$ or an aerogenic SiO$_2$-Al$_2$O$_3$ mixture already show a space-time yield which is increased by about 20%. Surprisingly, it has now been found that when the said aerogenic starting material is used, cylindrical particles with curved front faces produce a space-time yield which is further considerably increased in comparison with regular cylinders.

The invention relates to a process for the preparation of vinyl acetate in the gas phase from ethylene, acetic acid and oxygen or oxygen-containing gases on a catalyst which contains palladium and/or compounds thereof and if appropriate additionally gold and/or gold compounds and, as activators, alkali metal compounds and if appropriate additionally cadmium compounds, on a support which consists of aerogenic SiO$_2$ or an aerogenic SiO$_2$-Al$_2$O$_3$ mixture having a surface area of 50–250 m$^2$/g and a pore volume of 0.4–1.2 ml/g, the pore volume being formed to the extent of at least 50% by pores having a diameter of 50–200 Ångströms, wherein the support consists of cylindrical particles having curved front faces.

The aerogenic oxide or oxide mixture used for the preparation of the cylindrical support particles is prepared, for example, by flame hydrolysis of silicon tetrachloride or a silicon tetrachloride-aluminum trichloride mixture in an oxyhydrogen flame. The vitreous "microbeads" thus obtained have a surface area of 100–300 m$^2$/g. Microbeads (commercially available under the name ®Aerosil) having a surface area of 150 to 200 m$^2$/g and consisting of 97% by weight of SiO$_2$ and 3% by weight of Al$_2$O$_3$ are particularly suitable.

The microbeads can be processed to the cylindrical particles used according to the invention by a procedure in which, for example, the microbeads are made into a paste with a dilute solution of a mineral size, the paste is brought into the desired cylindrical shape (with curved front faces) by pressing and the size is converted into a sparingly soluble form by calcining. Examples of possible inorganic sizes are waterglass, silicic acid sol, aluminum oxide sol, kaolin and bentonite, kaolin in amounts of 1–20% by weight, in particular 3–10% by weight, being preferred.

After pressing, the cylindrical particles are calcined, a pore volume of 0.4–1.2 ml/g and a surface area of 50 to 250 m$^2$/g being formed. The pore volume here is formed to the extent of at least 50% by pores having a diameter of 50–200 Ångströms. Surface areas of 70 to 150 m$^2$/g are particularly favorable. The size of the surface area depends on the calcining temperature and duration. The higher the temperature and the longer the calcining time, the smaller the surface areas become.

By using the cylindrical support particles having curved front faces, it is possible to produce a substantial increase in the space-time yield of the catalysts for the same content of active substances and the same reaction conditions without the selectivity suffering. The advantages of the process according to the invention are that the amount of catalyst and reactor volumes in new plant can be reduced by this increase in performance, which leads to a considerable reduction in plant costs, or that the capacity of already existing plants can be substantially increased without conversion work, and the investment costs for extending the plant are thus saved. However, instead of this, it is also possible to leave the space-time yield unchanged and then to achieve a considerably reduced formation of CO$_2$ and thus a higher selectivity for the same space-time yield in comparison with conventional catalysts, which means that significant amounts of ethylene are saved.

The surface area of the supports mentioned is always the so-called BET surface area measured by the method of Brunauer, Emmett and Teller. It gives the total surface area of 1 g of support material, that is to say the sum of the external surface area of the support and of the surface area of all the open pores. The total pore volume and the proportion thereof to which pores of a certain size (for example those having a diameter of 50–200 Ångströms) contribute can be measured with the aid of mercury porosimetry.

The dimensions of the cylindrical particles are preferably chosen so that on the one hand easy filling of the reactor with the support is ensured (that is to say exclusion of extremely large particles), and on the other hand there is no great drop in pressure (that is to say exclusion of extremely small particles). The cylindrical particles in general have a radius of 2–8 mm, preferably 2–4 mm. The length of the cylindrical particles (including the curved front faces) is 2 to 15 mm, preferably 6 to 15 mm.

The height of each of the two curved front faces is 0.2 times to once the cylinder radius. The FIGURE shows the shape of the cylindrical particles; in this FIGURE, 1 denotes the length (including the curved front faces), r denotes the radius of the cylinder and h denotes the height of the curved front faces.

The shape of the cylindrical particles having a curved front face is comparable with the shape of known pharmaceutical capsules.

The catalytically active substances are applied to the support in the customary manner, for example by impregnation of the support with a solution of the active substances, subsequent drying and if appropriate reduction. However, the active substances can also be applied, for example, by precipitation onto the support or by spraying on, vaporizing on or dipping.

Suitable solvents for the catalytically active substances are above all unsubstituted carboxylic acids having 2 to 10 carbon atoms in the molecule, such as acetic acid, propionic acid, n- and iso-butyric acid and the various valeric acids. Acetic acid is preferably used as the solvent because of its physical properties and also for economic reasons. The additional use of an inert solvent is advantageous if the substances are not sufficiently soluble in the carboxylic acid. Thus, for example, palladium chloride can be dissolved considerably better in an aqueous acetic acid than in glacial acetic acid. Possible additional solvents are those which are inert and are miscible with the carboxylic acid. In addition to water, there may be mentioned, for example, ketones, such as acetone and acetylacetone, and furthermore ethers, such as tetrahydrofuran or dioxane, and also hydrocarbons, such as benzene.

The catalyst contains palladium and/or compounds thereof as the noble metal component and alkali metal compounds as the activator component. It can contain gold and/or compounds thereof as additional noble metal components and it can contain cadmium compounds as additional activator components.

Possible compounds of palladium are all those salts and complexes which are soluble (and if appropriate reducible) and do not leave any deactivating substances such as halogen or sulfur in the finished catalyst. The carboxylates, preferably the salts of aliphatic monocarboxylic acids having 2 to 5 carbon atoms, for example the acetate, the propionate or the butyrate, are particularly suitable. The nitrate, nitrite, hydrated oxide, oxalate, acetylacetonate and acetoacetate, for example, are furthermore suitable. However, compounds such as the sulfate and the halides can also be used if it is ensured that the sulfate residue is removed, for example by precipitation with barium acetate, or the halogen is removed, for example by precipitation with silver nitrate, before the impregnation, so that the sulfate or halogen anion does not get onto the support. Palladium acetate is the particularly preferred palladium compound because of its solubility and its accessibility.

The content of palladium in the catalyst is in general 1.3–3% by weight, preferably 1.5 to 2.5% by weight, in particular 2–2.5 % by weight, the metal content being based on the total weight of the supported catalyst.

As well as palladium and/or compounds thereof, gold and/or compounds thereof can also additionally be present. A particularly suitable gold compound is barium acetoaurate. Gold or one of its compounds, if it is used, is in general added in an amount of 0.2 to 0.7% by weight, the metal content being based on the total weight of the supported catalyst.

The catalyst contains alkali metal compounds and if appropriate additional cadmium compounds as activators. Examples of suitable activators are alkali metal carboxylates, such as, for example, potassium acetate, sodium acetate, lithium acetate and sodium propionate. Those alkali metal compounds which are converted into the carboxylates under the reaction conditions, such as, for example, hydroxides, oxides and carbonates, are also suitable. Possible compounds of cadmium are those which contain no halogen or sulfur, for example carboxylate (preferred), oxide, hydroxide, carbonate, citrate, tartrate, nitrate, acetylacetonate, benzoylacetonate and acetoacetate. Cadmium acetate is particularly suitable. Mixtures of various activators can also be used. Each individual activator is in general added in an amount of 0.5 to 4% by weight, the metal content of the activator being based on the total weight of the supported catalyst.

The following catalysts are preferred: palladium/alkali metal element/cadmium and palladium/gold/alkali metal element, it being possible for the palladium and gold to be present in the finished catalyst as metals or compounds and potassium being preferred as the alkali metal element (in the form of a carboxylate). The K:Pd or K:(Pd+Au) ratio here is preferably 0.7:1 to 2:1. The Cd:Pd or Cd:(Pd+Au) ratio is preferably 0.6:1 to 2:1, in particular 0.6:1 to 0.9:1. Pd, Au, Cd and K here are always calculated as the elements, that is to say, for example, only the metal contents of Pd acetate, Cd acetate and K acetate on the support are compared with one another. The catalysts palladium acetate/potassium acetate/cadmium acetate and palladium acetate/barium acetoaurate/potassium acetate are particularly preferred.

The impregnation of the catalyst support with the solution of the active components is preferably carried out by a procedure in which the support material is covered with a layer of the solution and the excess solution is then poured off or filtered off. Taking into account solution losses, it is advantageous only to use the solution corresponding to the integral pore volume of the catalyst support and to mix the components thoroughly so that all the particles of the support material are uniformly wetted. This mixing can be achieved, for example, by stirring. It is advantageous to carry out the impregnation operation and the mixing at the same time, for example in a rotating drum or a drum drier, it being possible for drying to follow immediately. It is furthermore advantageous to choose the amount and composition of the solution used for impregnating the catalyst support so that it corresponds to the pore volume of the support material and the desired amount of active substances is applied by a single impregnation.

The catalyst support impregnated with the solution of the active substances is preferably dried under reduced pressure. The temperature during drying should be less than 120° C., preferably less than 90° C. It is moreover in general advisable to carry out the drying in a stream of an inert gas, for example in a stream of nitrogen or carbon dioxide. Te residual content of solvent after drying should preferably be less than 8% by weight, in particular less than 6% by weight.

If reduction of the palladium compounds (and if appropriate of the gold compounds) is carried out, which can sometimes be beneficial, this can be performed in vacuo, under normal pressure or under an increased pressure of up to 10 bar. It is advisable here for the reducing agent to be diluted to a greater degree with an inert gas the higher the pressure. The reduction temperature is between 40° and 260° C., preferably between 70° and 200° C. It is in general advantageous for an inert gas-reducing agent mixture which contains 0.01 to 50% by volume, preferably 0.5 to 20% by volume, of reducing agent to be used for the reduction. Nitrogen, carbon dioxide or a noble gas, for example, can be used as the inert gas. Possible reducing agents are, for example, hydrogen, methanol, formaldehyde, ethylene, propylene, isobutylene, butylene and other olefins. The amount of reducing agent depends on the amount of palladium and if appropriate on the gold employed; the reduction equivalent should be at least 1 to 1.5 times the oxidation equivalent, but larger amounts of reducing agent do no harm. For example, at least 1 mole of hydrogen should be used per mole of palladium. The reduction can be carried out after the drying, in the same plant.

The vinyl acetate in general prepared by passing acetic acid, ethylene and oxygen or oxygen-containing gases over the finished catalyst at temperatures of 100° to 220° C., preferably 120° to 200° C., under pressures of 1 to 25 bar, preferably 1 to 20 bar, it being possible for unreacted components to be recycled. The oxygen concentration is advantageously kept below 8% by volume (based on the acetic acid-free gas mixture). Under certain circumstances, however, dilution with inert gases, such as nitrogen or carbon dioxide, is also advantageous. $CO_2$ in particular is suitable for dilution in circulation processes, since it is formed in small amounts during the reaction.

The following examples are intended to illustrate the invention.

Comparison Example 1 (spherical support particles of conventional non-aerogenic $SiO_2$)

500 g (=1 l) of a silicic acid support which had been pressed to beads 5–6 mm in diameter from calcined bentonite which had then been washed with HCl ($SiO_2$ content after this washing 96% by weight) were used. The support of these spherical particles had a BET surface area of 128 $m_2/g$ and a total pore volume of 0.77 ml/g, formed to the extent of 33% by pores having a diameter of 50–200 Ångströms. The support was impregnated with a solution (corresponding to this pore volume) of 20 g of Pd acetate, 14.5 g of Cd acetate and 18.5 g of K acetate in 340 ml of glacial acetic acid and was dried at 60° C. under nitrogen under a pressure of 270 mbar to a solvent residual content of 2% by weight. This resulted in a doping of 1.7% by weight of Pd, 1.1% by weight of Cd and 1.4% by weight of K (Cd:Pd =0.65:1, K:Pd=0.82:1).

A reaction tube of 8 mm internal diameter and 1.5 m in length was filled with 50 ml of the finished catalyst. The gas to be reacted was then passed over the catalyst under a pressure of 8 bar (reactor intake) at a catalyst temperature of 142° C. At the reactor intake, this gas consisted of 27% by volume of ethylene, 55% by volume of $N_2$, 12% by volume of acetic acid and 6% by volume of $O_2$. The results can be seen from the table.

Comparison Example 2 (cylindrical support particles with flat front faces, prepared from an aerogenic $SiO_2$-$Al_2O_3$ mixture)

500 g (=1 l) of an aerogenic oxide mixture of 97% by weight of $SiO_2$ and 3% by weight of $Al_2O_3$ (commercially available under the name ®Aerosil MOX 170) were pressed to cylindrical support particles with flat front surfaces with the aid of kaolin and the particles were then dried. After subsequent calcining, the particles had a radius of 2.5 mm and an average length of 5 mm, and their BET surface area was 139 $m^2/g$. The particles had a total pore volume of 0.75 ml/g, formed to the extent of 78% by pores having a diameter of 50–200 Ångströms. The support particles were impregnated and dried as in Comparison Example 1, so that the same doping was present. The catalyst was then tested as in Comparison Example 1. The results can be seen from the table.

Example (cylindrical support particles with curved front faces, prepared from an aerogenic $SiO_2$-$Al_2O_3$ mixture)

500 g of the aerogenic oxide mixture mentioned in Comparison Example 2 were pressed to cylindrical support particles which, in contrast to Comparison Example 2, had curved front faces. After calcining, the particles had a radius of 3 mm and an average length of 6.5 mm (including the two curved front faces); the height of the two curved front faces was in each case 1 mm. The particles had a BET surface area of 126 $m^2/g$ and a total pore volume of 0.74 ml/g, which was formed to the extent of 77% by pores having a diameter of 50–200 Ångströms. The support particles were impregnated and dried as in Comparison Examples 1 and 2, so that the same doping was present. The catalyst was then tested as in Comparison Examples 1 and 2. The results can be seen from the table.

|  | Comparison Example 1 | Comparison Example 2 | Example |
| --- | --- | --- | --- |
| Support material | Non-aerogenic $SiO_2$ | Aerogenic $SiO_2$—$Al_2O_3$ mixture | Aerogenic $SiO_2$—$Al_2O_3$ mixture |
| Shape | Beads | Cylinders with flat front faces | Cylinders with curved front faces |
| Selectivity | 92% | 93% | 94% |
| Space/time yield | 400 g/liter.hour | 542 g/liter.hour | 640 g/liter.hour |

We claim:

1. A process for the preparation of vinyl acetate in the gas phase from ethylene, acetic acid and oxygen or oxygen-containing gases on a catalyst which contains palladium and/or compounds thereof and optionally gold and/or gold compounds and, as activators, alkali metal compounds and if optionally cadmium compounds, on a support which consists of aerogenic $SiO_2$ or an aerogenic $SiO_2$-$Al_2O_3$ mixture having a surface area of 50–250 $m^2/g$ and a pore volume of 0.4–1.2 ml/g, the pore volume being formed to the extent of at least 50% by pores having a diameter of 50–200 Angstroms, wherein the support consists of cylindrical particles having curved front faces.

2. The process as claimed in claim 1, wherein the cylindrical particles with a curved front face have a radius of 2–8 mm and a length, including the curved front faces, of 2–15 mm, the height of each of the two curved front faces being 0.2 times to once the radius.

3. The process as claimed in claim 1, wherein the cylindrical particles with a curved front face have a radius of 2–4 mm and a length, including the curved front faces, of 6–15 mm, the height of each of the two curved front faces being 0.2 times to once the radius.

* * * * *